US009278452B2

(12) United States Patent
Brandenberger (10) Patent No.: US 9,278,452 B2
(45) Date of Patent: *Mar. 8, 2016

(54) PROCESS FOR FINDING A PATH IN AN AUTOMATED HANDLING SYSTEM, AND HANDLING SYSTEM WITH CORRESPONDING CONTROL MODULE FOR FINDING A PATH

(71) Applicant: Tecan Trading AG, Mannedorf (CH)

(72) Inventor: Joel Brandenberger, Au (CH)

(73) Assignee: TECAN TRADING AG, Mannedorf (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/638,668

(22) Filed: Mar. 4, 2015

(65) Prior Publication Data
US 2015/0251315 A1 Sep. 10, 2015

(30) Foreign Application Priority Data
Mar. 10, 2014 (CH) .......................... 350/14

(51) Int. Cl.
| G05B 19/18 | (2006.01) |
| B25J 9/16 | (2006.01) |
| B25J 9/00 | (2006.01) |
| G05B 19/4061 | (2006.01) |
| G01N 35/00 | (2006.01) |
| G01N 35/10 | (2006.01) |
| G01N 35/04 | (2006.01) |

(52) U.S. Cl.
CPC .............. *B25J 9/1676* (2013.01); *B25J 9/0087* (2013.01); *B25J 9/1666* (2013.01); *G01N 35/0099* (2013.01); *G05B 19/4061* (2013.01); *G01N 35/10* (2013.01); *G01N 2035/0491* (2013.01); *G05B 2219/39083* (2013.01); *G05B 2219/40497* (2013.01); *Y10S 901/14* (2013.01); *Y10S 901/49* (2013.01)

(58) Field of Classification Search
CPC ...... B25J 9/1676; B25J 9/0087; B25J 9/1666; G01N 35/10; G01N 2035/0491
USPC ........................................................ 700/255
See application file for complete search history.

(56) References Cited

U.S. PATENT DOCUMENTS

| 5,491,638 A * | 2/1996 | Georgi ............... G05B 19/4061 700/195 |
| 2014/0025204 A1* | 1/2014 | Schlaich ................ B25J 9/1676 700/255 |

* cited by examiner

*Primary Examiner* — Ian Jen
(74) *Attorney, Agent, or Firm* — Notaro, Michalos & Zaccaria P.C.

(57) ABSTRACT

An Automated handling system has a working area, at least one object in the working area, at least a first numerically controlled arm and at least a second numerically controlled arm. The arms are movable above the working area and have a collision avoidance mechanism. The current actual topography of the working area is determinable, a movement planning algorithm determines a path from a first position to a second position, wherein in the first application of the movement planning algorithm a reference path, a quasi-static collision examination for the path, which has been provided by the movement planning algorithm, is applicable, a dynamic collision examination for the path, which has been suggested by the movement planning algorithm, is applicable, and wherein the collision examination determine whether, when moving the first arm a collision would be provoked.

26 Claims, 7 Drawing Sheets

PROCESS FOR FINDING A PATH IN AN AUTOMATED HANDLING SYSTEM, AND HANDLING SYSTEM WITH CORRESPONDING CONTROL MODULE FOR FINDING A PATH

RELATED PATENT APPLICATIONS

This patent application claims priority of the Swiss patent application No. 00350/14, filed on Mar. 10, 2014. The whole content of this priority application is herein incorporated in its entirety by reference.

RELATED FIELD OF TECHNOLOGY

The invention relates to processes for finding a path in an automated handling system as well as to handling systems having a corresponding control module for finding a path. In particular, the invention relates to the path finding in computer-controlled liquid handling systems.

BACKGROUND OF THE INVENTION

There are several medical, biological, chemical and pharmaceutical devices which are concerned with the handling and use of liquids. For example, there are automated liquid handling systems for carrying out medical, biological, physical and chemical investigations or to carry out processes in these areas.

Today, most of the automated liquid handling systems are so called computer-controlled handling systems.

A typical computer-controlled handling system comprises a working area (working table) for placing containers for liquids, a motorized pipetting robot and a controller (mostly a processor-based controller). The pipetting robot comprises at least one pipette for aspirating and dispensing liquid probes. By the use of a sequence program, which is carried out in the controller, the pipetting robot may be moved to a defined position for carrying out a specific action there. For example, in this way a pipette may be lowered into a container for aspirating a liquid or for dispensing a liquid there.

Modern handling systems comprise more than only one robot. It may be very complex in such systems to define the single courses of movements in such a way that no collision or mutual impairments occurs.

A simple approach would be the application of a learning process (so called teach-in) where the single robotic arms are moved manually, thereby defining the desired actions. However, such a teach-in process soon reaches its limits e.g. when an entire process shall be optimized.

For avoiding collisions in robotic systems, mathematical methods may be used for assessing collisions. Numerous publications exist here.

In the end, it may be concluded from the theoretical observations that it is very difficult and complex to compare the different collision procedures with each other. This is mainly based on the fact that the different collision procedures are very sensitive with respect to specific scenarios and constellations.

Thus, there is the problem to configure the controller of a multi-axial handling system as flexible and productive as possible, wherein a collision avoidance for single, moving arms of such a handling system shall be carried out as fast as possible.

OBJECT AND SUMMARY OF THE PRESENT INVENTION

According to the invention, a process for avoiding collisions in an automated handling system is provided the features of which may be taken from claim 1.

According to the invention, an automated handling system with collision avoidance is provided the features of which may be taken from claim 15.

Advantageous embodiments may be taken from the respective dependent claims.

The collision avoidance may comprise in all embodiments a process or module for finding a path and a process or module for examining collisions.

The invention particularly relates to the avoidance of collisions in a laboratory- or medical engineering handling system. In particular, it relates to liquid handling systems, e.g. such as pipetting robots.

It is the aim of the invention to find a suitable solution in form of a suitable path for each movement request in such systems and thereby to exclude collisions or other impairments.

The present invention relates to the avoidance of collisions in a dynamic environment, as there are at least two moving arms which have to be considered. The system of the invention is based on a so-called known quasi-static environment. The environment is formed by the working table with all objects thereon and eventually present additional mountings on the working table for peripheral devices such as incubators, microplate readers or microplate logistic devices. As all objects in the motion area of the arms are provided in form of modelled envelopes, the actual topography may be determined in each case. The environment is termed being a quasi-static environment as it does not or does only marginally change within a time frame (e.g. during the movement of an arm from A to B).

As mostly, the movements are carried out not multiple times but once and directly, a solution is provided in form of a real-time implementation for avoiding collisions in the handling system.

According to the invention, preferably all embodiments comprise a point-to-point path finding within the context of the collision avoidance. This point-to-point path finding is carried out by taking at least two arms into account, which may be moved in the system with each other and/or relative to each other, that is, beside the quasi-static also dynamic relations are considered.

Preferably in all embodiments a coordination between the arms is used, however there is no cooperation of the arms. An example for this is, when one arm is holding a microtiter plate while another arm is pipetting into this microtiter plate. As this is not the core of the invention, the arms in most of the embodiments have a simple coupling between each other, which is achieved by a controller or a control module of the system.

This simple coupling is preferably used in all embodiments for "telling" an arm, that also another arm is moved or is about to be set in motion. Thus, when finding a path for one arm, the movement of the other arm has to be taken into account as well, and in these cases also a dynamic collision examination has to be carried out beside the quasi-static examination.

According to the invention, a heuristic approach is used preferably in all embodiments, as this approach provides most rapidly results while producing relatively optimal paths.

In certain scenarios, the heuristic approach of the invention could not find a solution, although in theory, there is a possible way. For such special cases, in all embodiments of the invention additional rules may be applied optionally.

Where necessary, according to the invention evasion strategies may be provided which for example account for the single applications. In those embodiments, in which such evasion strategies are used, these evasion strategies are calculated to be available for use in the device/the system.

The invention allows the use of evasion strategies which e.g. ensure that important steps (steps having a high priority) take precedence over less important steps. Such evasion strategies may be fixedly provided in all embodiments of the invention. However, such embodiments are possible as well in which evasion strategies may be fixedly set or may be selectable. This may be achieved for example by the use of a logical priority switch.

The invention allows the use of evasion strategies which ensure e.g. that delicate steps (steps with high priority) are carried out with particular care, for example to avoid dripping of a drop out of a pipette, thereby contacting a critical probe on the working area. For this purpose, e.g. respective careful accelerations and/or evasion paths along not critical sectors may be provided.

The provision of careful accelerations and/or evasion paths by be realized in all embodiments by a firmware in the motor control of an arm or e.g. by rules in a control module.

In the present invention, the quality of the different movement planning algorithms is evaluated by the length of the respective paths and by the calculation time of the algorithm, to thereby find the best possible algorithm. Some of the algorithms which have been analyzed generated considerably longer paths compared to the optimal path for the respective scenario, while other algorithms used more (calculation) time for the collision examination than others.

Attention has been directed to the fact that the chosen algorithm produces results also in complex scenarios, where other algorithms have not found suitable solutions.

In view of the requirements which have to be fulfilled by a handling system of the invention, the algorithm which shall be used must provide results rapidly and as close as possible to the optimal path.

According to the invention a movement planning algorithm is used which is to be understood as a type of procedure. This procedure is based on one or more rules which are according to the invention given by the system.

Preferably in all embodiments a movement planning algorithm is used which comprises a set of rules having multiple rules, these rules being heuristic rules. The set of rules of the invention generates a sequence connection between single rules.

Preferably in all embodiments a movement planning algorithm is used for successively determining multiple possible pathways, which are placed/stored consecutively in a list or table. In a subsequent partial process, one pathway after the other is provided from the table or list and is subjected to a collision examination. As soon as a collision free path has been found, this process is interrupted. This approach is particularly efficient and provides repeatedly the same results.

The present invention may not only be used in proprietary handling systems but additionally in open handling systems of various providers.

The handling systems according to the invention have the advantage that the space above the working area may be used in an optimal manner and that very narrow and precise movements are executable.

A particular advantage of the invention is based on unraveling into a quasi-static collision examination and a dynamic collision examination, as this unraveling provides rapid and reliable results.

BRIEF DESCRIPTION OF THE DRAWINGS

The handling systems according to the invention and the processes according to the invention will now be explained in detail by reference to schematic drawings which do not restrict the scope of the invention.

DETAILED DESCRIPTION OF THE PRESENT INVENTION

In the following, liquid handling systems 100 will be described by way of example, whereby the invention may be applied without problems also to other handling systems 100. The handling systems 100 are denominated in the following in short as systems 100.

Figure 1:
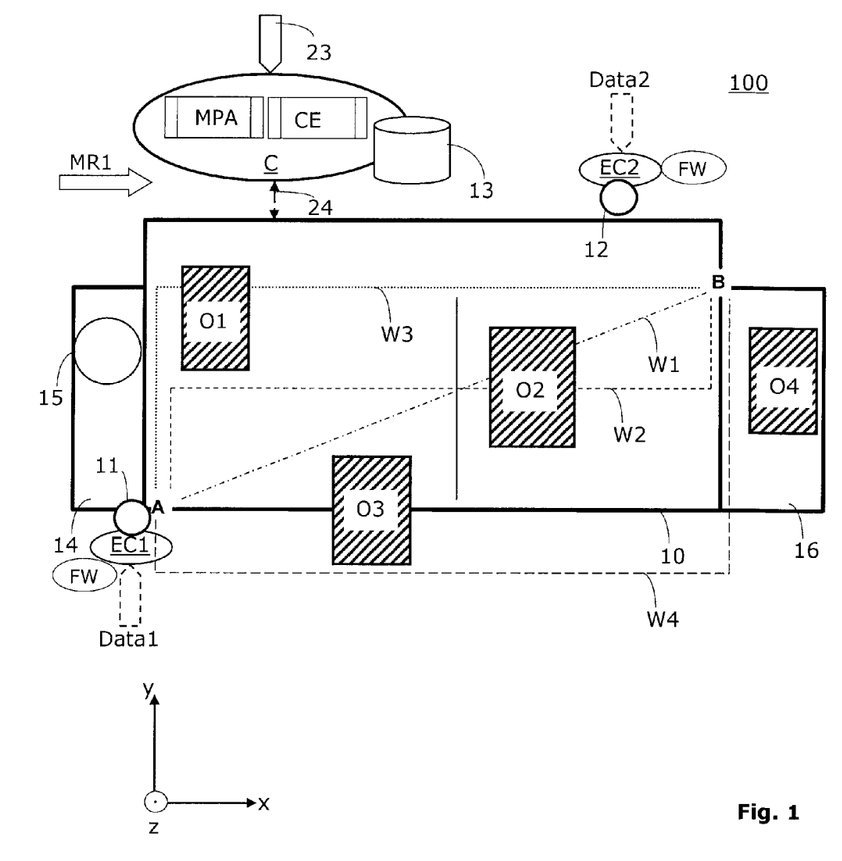
FIG. 1 shows a schematic top view on a first handling system of the invention with two arms and with several objects.

The FIG. 1 shows a system 100 which here comprises a working area 10 being arranged essentially horizontally and configured for quasi-statically placing at least one (liquid) container O1. In FIG. 1 a situation is shown in which in total four container O1-O4 or other objects are arranged on the working area 10. The system 100 further comprises at least two numerically controlled (handling) arms 11, 12, which are here depicted as simple circles. These two arms 11, 12 are movable over the working area 10. For this purpose each of the two arms 11, 12 has an own drive system, so that both arms 11, 12 are movable spatially and temporally independent from each other.

In FIG. 1 and the other Figures, the driving systems are represented by an engine control EC1 and EC2, which typically comprises a firmware FW.

Labware such as microplates, wells, carrier, frames, tubes, container, bottles, flasks and the like as well as balances, shaker, incubators, carrier for labware, thermocycler devices and the like are here referred to as objects O1-O4 for simplicity reasons.

A system of the invention comprises at least two arms 11, 12, wherein at least one arm 11 of them comprises at least three motion degrees of freedom.

One arm 12 may e.g. pipette and dispense liquids. Another arm 11 may comprise e.g. grippers, so that this arm 11 may grip and move a microplate. Such a microplate is an object which serves as a working plate and which has multiple cavities for receiving liquids.

Preferably in all embodiments arms 11, 12 are used which are movably positioned above the working area 100 in a so-called portal- or bridge-configuration, as shown e.g. in the FIGS. 3A, 3B and 4A to 4C. The arms 11, 12 may e.g. be mounted on a guide rail or bridge 17 above the working area 10. Each of the arms 11,12 may e.g. comprise a carriage 19, which has a drive for moving the respective arm 11,12 along the guide rail or bridge 17 or which is movable by an external drive (e.g. by a belt drive).

The drive of each arm comprises an engine control EC1 or EC2, respectively, which is realized as a combination of hard- and software. As hardware, such an engine control EC1 or EC2 preferably comprises a controller and a drive control electronic, which applies power or voltage to the engine of the drive. The application/impression of an electric current or a voltage is shown in the Figures by a dashed double arrow 25. The double arrow 25 shall indicate that in most cases the drive provides a feedback (e.g. information on positions or rotational speed) back to the engine control EC1, EC2. The software is typically accomplished as a firmware FW. By the firmware FW, motion profiles (parameters such as electric current data, step precision, and e.g. distance, speed, ramp, breaks, and loops) may be provided. Such settings, which are implemented in the firmware FW, are also referred to as movement characteristic.

The firmware FW may also be configured in all embodiments as a profile generator which defaults the exact movement sequences. Preferably, this profile generator cooperates in all embodiments not only with the drives but also with the path finding, so that in the planning of the pathway and/or collision examination, the exact pathway may be considered.

The engine control EC1, EC2 quasi serves as an interface between the control S and the motor(s) of an arm 11, 12. The actual movement generation is effected by the engine control EC1, EC2 and is essentially defined by default settings in the firmware FW or the profile generator. It is important to note here that a concrete movement carried out by an arm 11, 12 is merely an approximation to the reference movement, as due to e.g. the engine characteristic, the inertia and (stress-involved) tolerances of the arms 11, 12, smaller, system inherent deviations may occur (also called contouring errors).

According to the invention, this fact is accommodated insofar as already in the pathfinding, the given deviations are considered. That is, according to the invention, already within the scope of the pathfinding, the exact process of movement of the arms 11, 12 is determined in advance in due consideration of the given default movement profile.

To allow this, the movement characteristics of the movement generation are considered in the planning of the movement MPA and/or in the collision examination CE.

Preferably, the controller C comprises in all embodiments an image of the firmware FW* of the respective engine controls EC1 and EC2, or the controller C has in all embodiments access to the profile generator. The term image FW* has been chosen to describe in particular the following possibilities of implementation:
- a true copy of the firmware FW;
- a transformation of the firmware FW into another programming language or -environment;
- a compilation of the firmware FW;
- an emulation of the firmware FW.

The controller C may comprise in all embodiments per engine control EC1, EC2 a corresponding image of the firmware FW* of these engine controls EC1, EC2. This image FW* is implemented into the controller C or is provided to the controller C in such a way that already when planning the path using the algorithm MPA and/or in the collision examination CE the influences of the firmware FW on the precise process of movement are considered.

Preferably, the controller C has in all embodiments access to the profile generator, so that already in the path planning using the algorithm MPA and/or in the collision examination CE the concrete movement process (that is the pathway as exact as possible) may be considered.

Figure 2A:
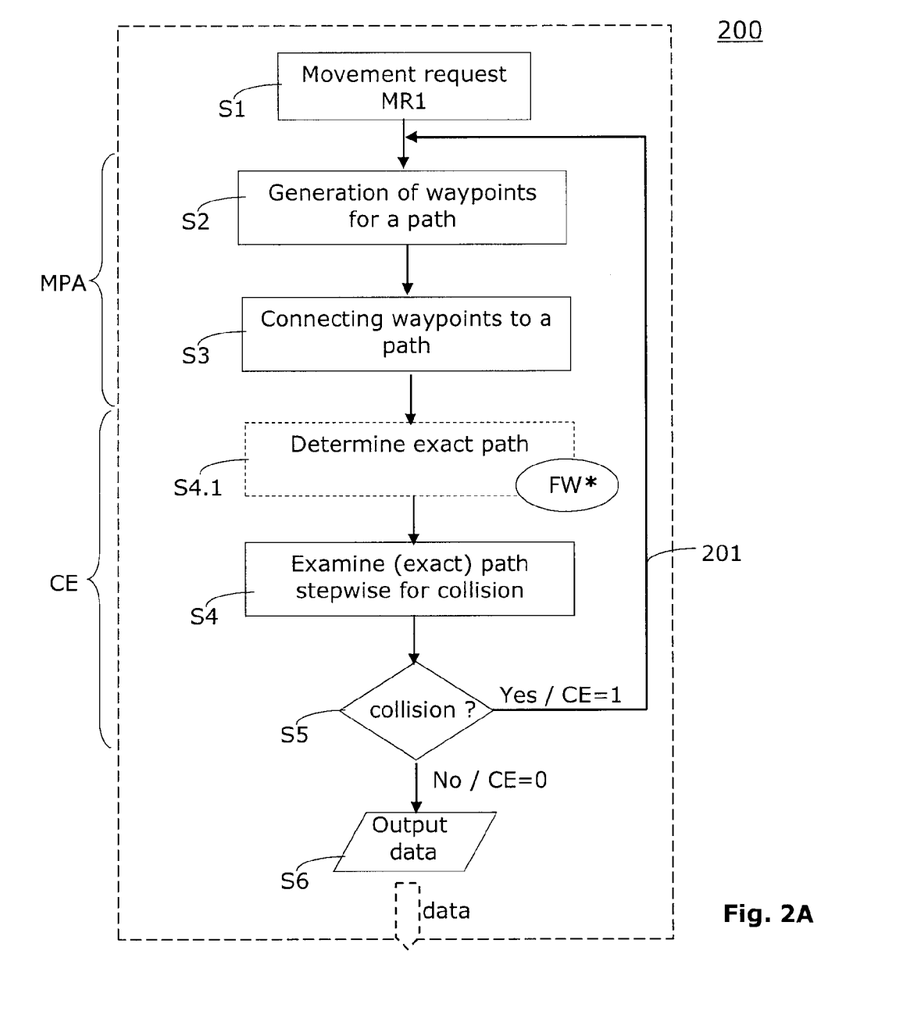
FIG. 2A shows a schematic flowchart of a first process of the invention.

Those embodiments are preferred in which the image FW* is used in the collision examination CE. From the waypoints, which are e.g. provided in a step S3 of the process 200, then the exact path covered by each arm 11, 12 is determined by use of the image FW*. This step is shown as an optional step S4.1 in FIG. 2A. To show that within the scope of the step S4.1 the image FW* is used, this image FW* of FIG. 2A is indicated by an oval.

Particularly preferred are embodiments in which output values of the profile generator are used in the collision examination CE.

The term of the exact path is used to indicate that a path, which has been determined by use of an image of the firmware FW* or of the profile generator, is lying considerably closer to the effective way of an arm 11, 12 than the path which has only been found by use of an algorithm MPA. The term "exact" is thus to be understood as a relative statement.

Then, preferably within the context of a preview, each arm 11, 12 is moved step by step along its exact path, to examine this exact way step by step in a pure mathematical approach in view of collisions (steps S4 and S5 of the process 200).

In case the optional step S4.1 is used within the scope of the process 200, then not the simple path is used in the collision examination in step S4, which has been provided by the algorithm MPA in step S3, but instead the exact path is used, which has been provided by the step S4.1. The optional step S4.1 may be applied as well in the process of the FIGS. 2C and 2D.

Within the scope of such a preview, not only the movement of an arm 11 relative to the object(s) O1-O4 are observed and examined in view of possible collisions, but additionally the movement of the arm 11 relative to the arm 12 and the movement of the arm 12 relative to the object(s) O1-O4.

The control module C may be in all embodiments part of the system 100. The control module C however may be as well in all embodiments an external element, which is connected with the system 100 by way of communication technology (e.g. by an interface 24).

Preferably, the control module C comprises in all embodiments for each arm 11, 12 a distinct module or an arm manager, which carries out individually for each arm a pathfinding in analogy to the process 200 of FIG. 2A. Each of this module or each of this arm manager, respectively, comprises an image of the firmware FW* of the corresponding arm or a respective profile generator.

In the Figures, the control lines are not shown or only adumbrated, as these are only schematic representations which serve to describe and show the invention. It is sufficiently known how to connect a controller with the single components and arms of a handling system 100.

The planning of the movement(s) in the system 100 is carried out by use of a so-called movement planning algorithm MPA. After or during the planning of a movement, which is carried out by use of the movement planning algorithm MPA, a collision examination CE is applied. In case this collision examination KP does not lead to the expectation of a collision, then the respectively planned movement may be transferred to the system 100, or to the engine control EC1, EC2 of the respective arm 11, 12 for execution. Otherwise, the movement planning algorithm MPA may be used again to determine an evasion path. This evasion path will then be subjected to the collision examination CE. These partial steps may be repeated until an evasion path has been found which is free of collisions. Processes 200 according to this principle may exemplarily be taken from the FIGS. 2A and 2B. An exemplified process where a collision examination CE is carried out after the use of the movement planning algorithm MPA is shown in the FIGS. 2C and 2D.

A preferred embodiment covers additionally the following approach. In case one of the two arms is not moving, and a collision occurs with the other arm, an evasion movement may be defaulted for the arm which is not moved. In case a collision occurs when two arm are moved in a planned manner, a time delay is provided to one of the arms (e.g. to the arm having a lower priority or to the arm having received the movement request later than the other arm). If the collision examination CE still indicates a collision of the arms, then a new route will be planned for one of the arms (e.g. for the arm having a lower priority or for the arm having received the movement request later than the other arm). In case one of the arms is currently occupied (e.g. carries out a pipetting process), the planning of the path for the other arm may be paused until the other arm has completed its work (e.g. the pipetting) and is moved away.

The principle of this process 200 is shown in FIG. 2A with the help of a schematic flow chart. In a first step S1, a first movement request MR1 is delivered to the system 100 or to the module C, as shown in FIG. 1 by a block arrow MR1. By using the movement planning algorithm MPA, waypoints are given as default in step S2, and in step S3 these waypoints are connected to a (simple) path.

The process 200 of the invention comprises in the case of the FIG. 2A a loop 201 (from S5 to S2), which typically is passed through multiple times, until a suitable path has been determined. Thus, in the most embodiments, the shortest path W1 or another reference path is defined when running through the step S2 (step c. of claim 1). Accordingly, it is firstly assessed whether the given reference path (e.g. the shortest path W1) is suitable. When the loop 201 is run through the next time, then other waypoints and thus another path (referred to as evasion movements W2, W3, W4) is given as a default and examined.

In all embodiments of the invention it is possible to provide at the beginning of the process 200 another path (e.g. by the controller C) instead of the shortest path W1 as a given default path. Such a path is denominated here as a reference path.

Now, each time when the loop 201 is passed through, the collision examination CE is used to assess the path of the steps S2, S3 and eventually step S4.1 for collisions in a stepwise manner. This step is denominated in FIG. 2A as step S4. In case the collision examination CE of step S4 has determined a collision (step S5 in FIG. 2A), the process 200 of FIG. 2A reaches back to the beginning, to give other waypoints as default. With these other waypoints, the steps S2, S3, eventually S4.1, S4 and S5 are repeated until the loop 201 in step S5 is completed with a "no". In case no collision is determined, it may be concluded that the path identified is suitable. This path is then outputted e.g. in form of a set of data (step S6 in FIG. 2A).

Figure 2B:
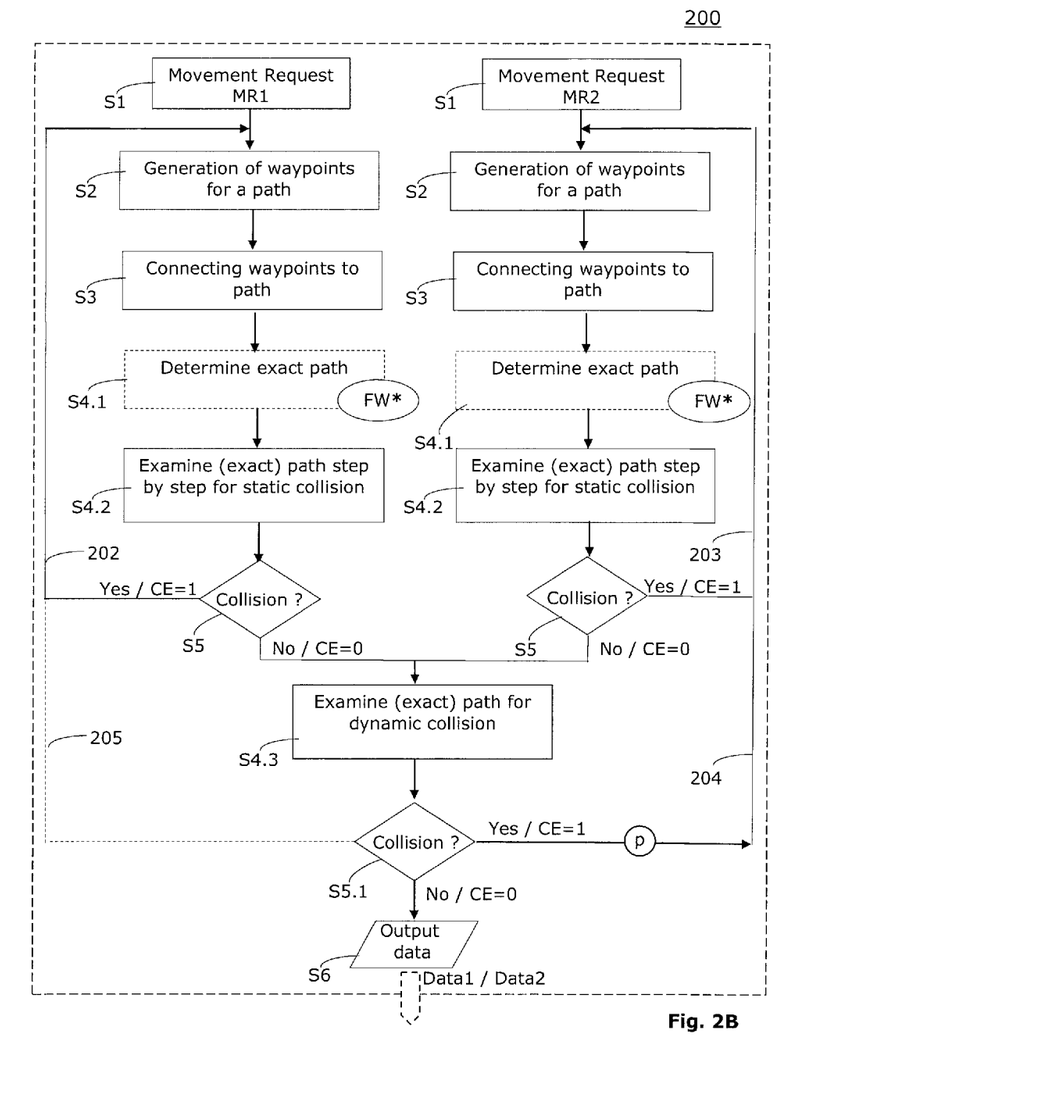
FIG. 2B shows a schematic flowchart of a second process of the invention.

Using FIG. 2B another process 200 of the invention is described. In principle, the processes 200 of the FIGS. 2A and 2B are analogue. The process 200 of FIG. 2B may be considered as being a further development or modification of the process 200 of FIG. 2A.

FIG. 2B shows a situation with two movement requests MR1 and MR2 (in each case named as steps S1). The movement request MR1 is directed to a first arm 11 and the movement request MR2 is directed to a second arm 12. As already mentioned, to each of the arms 11, 12 a separate module or a separate arm manager may be assigned to. Thus, in the flow chart of FIG. 2B, two parallel process breaches are shown. In the example presented, both of these parallel process breaches are nearly identical. They only differ from each other by the image FW* of the firmware, as each of the arms may (but not must) comprise another firmware FW, or they only differ from each other by the profile generator, which may be assigned to each arm (but not must).

The parallel process branches may be identical in all embodiments, but must not be identical.

As already described, in a first step S1, a first movement request MR1 or a second movement request MR2, respectively, is provided to the system 100 or to the module C. By use of the movement planning algorithm MPA waypoints for the first arm 11 are inputted as default in step S2, and in step S3, these waypoints are connected to a path for the first arm 11. In analogy, a path is determined as well for the second arm 12.

Preferably, the path finding for the second arm 12 is in all embodiments delayed until a suitable, collision-free path has been found for the first arm 11. The path which has been found for the first arm 11 is then in the pathfinding for the second arm 12 assumed to be fix.

If the optional steps S4.1 are used within the scope of the process 200 of FIG. 2B, not the simple path is used in the collision examination CE for the first arm 11 in step S4 and for the second arm 12 in step S4, which has been provided by the algorithm MPA in step S3, but instead, for each arm 11, 12 the exact path is applied, which has been provided in each case by the steps S4.1. For determining the exact path, in each case the image FW* of the firmware of each arm 11, 12 or the profile generator of these arms 11, 12 may be used.

Other than in FIG. 2A, in the process 200 of FIG. 2B for each arm 11, 12 a first collision examination CE.1 is carried out independently from each other (steps 4.2 and S5 in FIG. 2B). These first collision examinations CE.1 are named here as static collision examinations, as they relate the moving arm (e.g. arm 11) to quasi-static objects O1-O4. The term quasi-static here refers to the fact that the objects O1-O4 are not moved within the observation time frame, other than the arms 11, 12. In case a collision is predicted for one or both arms 11, 12, the process 200 is branched back to the respective step S2. Thus, if the planned (exact) path for arm 11 would lead to a collision with one of the objects O1-O4, the pathfinding would be carried out again for this arm 11. This is the purpose of the loop 202. For the second arm 12, the second loop 203 arranges that the steps S2, S3, S4.1, S4, S5 are repeated until no collision may occur.

Only when both arms 11, 12 are without collisions, then the arms 11, 12 will be analyzed relative to each other in this special embodiment. This second collision examination CE.2 is named as a dynamic collision examination, as here, the two moving arms (e.g. the arms 11, 12) are related to each other spatially and temporally. This second collision examination CE.2 is presented in FIG. 2B by the step S4.3. In this step S4.3 as well, the paths may be considered in all embodiments, which have been determined in step S3, or the exact paths of the optional steps 4.2 may be considered.

In case a collision of the two arms 11, 12 has been determined in the step S5.1, the process 200 may branch back to the beginning.

In all embodiments, this branching back may be controlled/influenced by a type of priority switch. In FIG. 2B such a switch (e.g. realized in form of a flag) is shown by the encircled symbol p at the right side of the step S5.1. One arm (e.g. arm 11) may have a higher priority than another arm (e.g. arm 12). In these cases it may be required in all embodiments that the pathfinding of the arm having a higher priority will not be interrupted, but that instead the pathfinding of the respective other arm will be carried out again for finding another suitable path. Such a switch however is preferably implemented in all embodiments in such a way that the path finding is not interrupted, but that instead the system ensures that the arm having the higher priority does not evade the other arm(s).

In FIG. 2B, the higher priority is exemplarily assigned to the first arm 11. Accordingly, the process 200 branches back to step S2 of the second arm, emanating from the step S5.1 (right column in the flow chart of FIG. 2B). The branch going back is indicated with the reference sign 204. The other branch back 205 is therefore indicated with a dashed line for the shown situation.

If no collision has been determined in step S5.1, this means that the found paths are suitable for both arms 11, 12. These paths are outputted in form of a data set (step S6 in FIG. 2B). The data (indicated in FIG. 1 as Data1 and Data2) may in all embodiments be outputted in step S6 separately for each arm 11, 12, and further submitted to the respective engine control EC1 or EC2.

The term "set of data" shall not be understood to be restrictive. It is about the output of data, parameters, or signals suitable to guide the respective arm 11 or 12 along the path which has been found in the process 200 and which has been categorized as being free of collisions. The data set preferably is in all embodiments directly compatible with the respective engine control EC1, EC2.

Figure 2C:
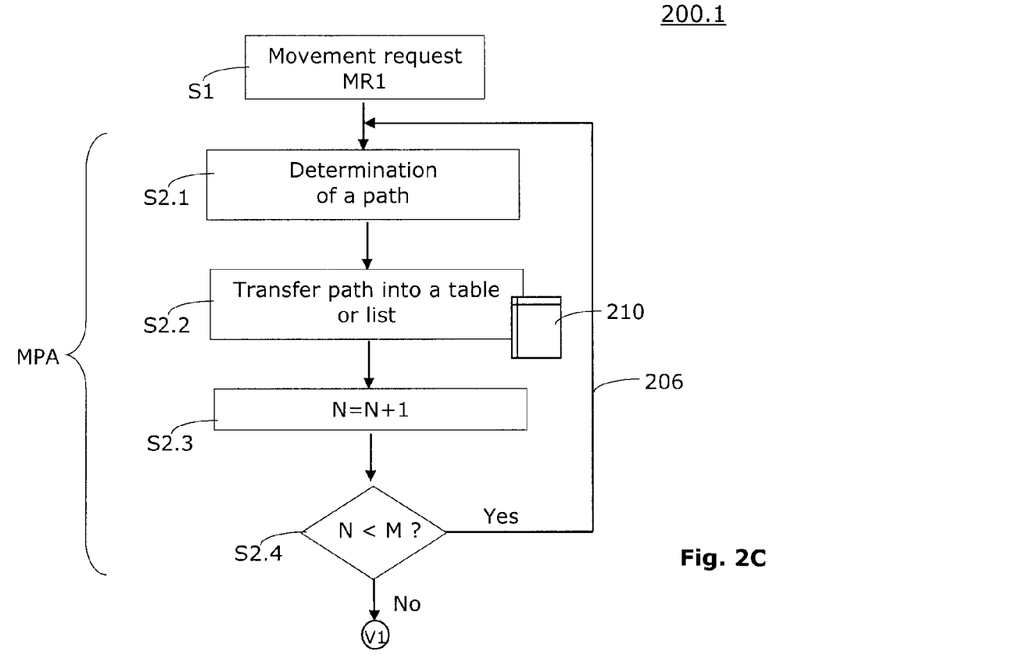
FIG. 2C shows a schematic flowchart of a first partial process of a third process of the invention.
Figure 2D:
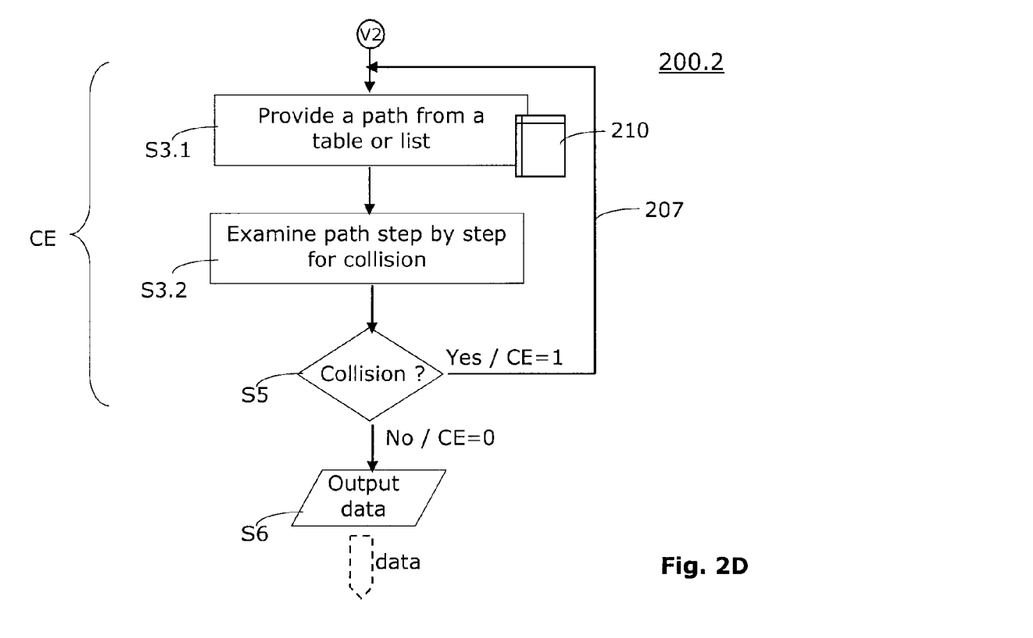
FIG. 2D shows a schematic flowchart of a second partial process of the third process of the invention.

In the FIGS. 2C and 2D another process 200 of the invention is shown, wherein FIG. 2C shows a partial process 200.1 and FIG. 2D shows a partial process 200.2. Preferably, these partial processes 200.1 and 200.2 are performed subsequentially.

After a movement request MR1 has been entered for an arm 11, a first path W1 is determined by applying a movement planning algorithm MPA (step S2.1 in FIG. 2C). This path W1 is put or stored, respectively, in a table or list (see reference sign 210 in the FIGS. 2C and 2D; step S2.2 in FIG. 2C). Then by way of example, an internal counter N is increased by 1 (step S2.3 in FIG. 2C). As long as N<M a loop is passed through. If N<M (step S2.4 in FIG. 2C), the trail 206 branches back to S2.1. As soon as N=M, the examination in step S2.4 results in a No and the process 200.1 ends at the point V1. N is a whole number which is increased respectively by increments of 1. M is a whole number which is used here to set the number of passes through the loop of the process 200.1. M may either be given fixedly, or may be defined by the user. The bigger M, the more possible paths will be determined and put into the table or list 210.

The table or list 210 may in all embodiments be realized e.g. in form of a (shifting) register in a storage. In an application according to the FIGS. 2C and 2D, such a (shifting) register works based on the First-In First-Out principle; that is the path which has been stored first will as well be subjected firstly to the collision examination in step S3.2 of FIG. 2D.

After M possible paths have been put into the table or list 210, the partial process 200.2 may succeed. This partial process 200.2 starts from point V2. Firstly, the first path is provided from the table or list 210 (step S3.1 in FIG. 2D). This first path is then examined stepwise with respect to collisions (step S3.2 in FIG. 2D).

This collision examination (step S3.2 in FIG. 2D) may comprise separately a static and a dynamic collision examination, or it may consider in one and the same collision examination (a so-called combined collision examination) both the quasi-static objects O1-O4 and the dynamic objects (e.g. the second arm 12).

A combined collision examination may e.g. be used as well in step S4 of FIG. 2A.

The steps S3.1, S3.2 and S5 are repeated until the loop 207 in step S5 terminates with a "No". If no collision was determined, the found path is suitable. This path then is outputted e.g. in form of a data set (step S6 in FIG. 2D).

Preferably, all collision examinations of the invention proceed according to the same principle. The path is dissected into pints, which in each case are away from each other by one step. Then for each of this points a collision inspection/calculation is done. With this collision inspection/calculation it is determined whether two objects (e.g. the arm 11 and the object O1) touch or penetrate each other. If the touch or penetrate each other, a collision exists and the respective path is condemned (discarded from the consideration). If no contact or penetration was detected, the arm 11 is moved further to the next point by one step, to repeat there the collision inspection/calculation.

These collision examinations according to the invention are preferably in all embodiments carried out with the envelope EH1, etc. for reducing the computing time. Usually it is sufficient for most of the embodiments when each envelope EH1 etc. is described by their edges and planes. If e.g. an edge of the envelope EH1 of the arm 11 penetrates a lateral plane of the object O1, then a collision exists.

Preferably, in all embodiments a heuristic approach is used for the movement planning algorithm MPA, as it has turned out to be faster and less computing intensive.

Figure 5:
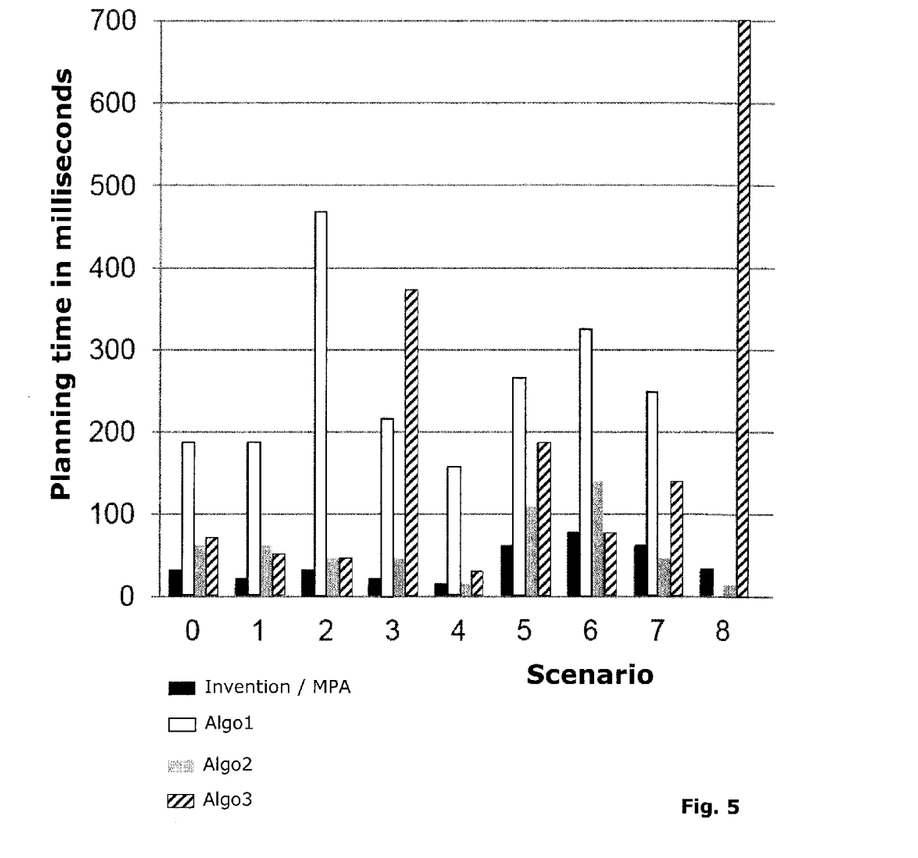
FIG. 5 shows a diagram in which four different algorithms are compared with respect to their planning time.

The selection of a heuristic approach as a movement planning algorithm MPA is based on numerous investigations and simulations. In FIG. 5 a graphic presentation of a comparison of four different algorithms is shown. In total, 9 different scenarios were investigated by simulation of these different movement planning algorithms. For each of these movement planning algorithms, named here with the terms invention (=MPA), Algo1, Algo2, and Algo3, the planning time was determined in milliseconds and presented in the graph of FIG. 5. The heuristic approach MPA of the invention is shown in black bars. The algorithm 1 (Algo1), shown in white bars, is a potential algorithm. In a potential algorithm, a potential field is used in the path finding. The approach of a potential field is that an attractive force is exerted from the target (here e.g. position B), which pulls the arm 11 towards it. Obstacles (e.g. O2) have a repulsive force. These potential fields may be compared with magnetic fields, which attract or retract the arm 11. When presenting the forces in a matrix, a net is achieved which has its minimum at the destination point B.

The algorithm 2 (Algo2), presented with the grey bars, is an RRTConnect-algorithm, and the algorithm 3 (Algo3), presented by shaded bars, is a PRM algorithm. In the scenario 8, no time may be seen for Algo1, as no path could be found in this scenario.

A RRTConnect-algorithm uses two trees, which are simultaneously generated from start A and target B. It is then tried to connect these trees for finding a path. RRT stands for Rapidly-exploring Random Trees. A PRM algorithm on the other hand generates a so called roadmap with points, which cover the whole movement area. These points and their connection are collision free. PRM stands for Probabilistic Roadmap Method.

The graph in FIG. 5 clearly shows the advantages of the heuristic MPA approach according to the invention versus the alternative solutions. In particular the control whether two arms 11, 12 would collide during evasion takes considerably longer time with the algorithms Algo2 and Algo3 compared with the algorithm MPA of the invention.

Analysis of the path length, carried out with the algorithm invention (=MPA), Algo1, Algo2, and Algo3 confirm the positive characteristics of the heuristic approach in connection with a (liquid) handling system 100 of the invention.

It has also been shown that the heuristic approach has the advantage of reproducibility, which is important in the field of laboratories and when repeatedly analyzing critical probes. The paths having been detected may be predicted, as because the manner how the paths are generated is always the same. Only such a validation allows carrying out e.g. DNA analysis using the systems 100.

According to this heuristic approach, rules or strategies for determining the pathways (e.g. for step S2 in FIG. 2A) are predefined as default. These rules or strategies are executed according to a given, fix sequence or according to a configurable sequence. Preferably, for each type of arm distinct rules or strategies are predefined in all embodiments, or these rules are connected for each type of arm to another set of rules.

Preferably, the rules or strategies are connected with each other to a such a set of rules, wherein the connections may be conditional. A simple example for a set of rules with connections is shown further below in this description.

In a portal or bridge system, which is preferably used in the invention, the following heuristically determined rule may be given as default (termed here Rule1):

The height (max_height in z-direction) of the highest object O1-O4 in the working area 10 is determined;
Then, the height difference between the current starting point A of the arm 11 and the max_height is determined;
This height difference is then provided as a waypoint to the movement planning (e.g. in step S2).

The Rule1 serves for a fast and safe determination of a relative evasion height ΔH which is suitable for guiding an arm 11,12 within the working area 10 without collisions above an object O1-O4.

In the following, further rules are given exemplarily, which have been determined heuristically. The herein described rules and strategies are examples which may be freely combined and/or adapted with each other. Additional rules and strategies may be added as well. Preferably, these rules and strategies are combined with each other to a set of rules, as mentioned above.

Rule2: When determining possible waypoints, so-called blocked areas are sorted out. In FIG. 1, on the left side of the working area 10 a blocked area 14 is shown exemplarily. In the system 100 e.g. a liquid tank 15 or the like may be positioned there. As typically this liquid tank 15 is present at the shown position in the blocked area 14, this blocked area 14 has been excluded from the planning of the path by the movement planning algorithm MPA.

Rule3: The movement planning algorithm MPA of the invention preferably works with all degrees of freedom of each arm 11, 12. This means that the movement planning algorithm MPA preferably takes all technically possible movements of the arms 11, 12 into account. However, to allow for a faster planning and finding of a path, it may be provided by an additional rule (named Rule3) which has been determined heuristically, that e.g. the movements in z-direction and in x-direction shall be preferred over the movements in the x-y-plane. As a result of Rule3 when used in the MPA, the movement planning algorithm MPA always tries to use a lifting or lowering movement parallel to the z-axis and translational movements parallel to the x-axis for finding an evasion path.

Figure 3A:
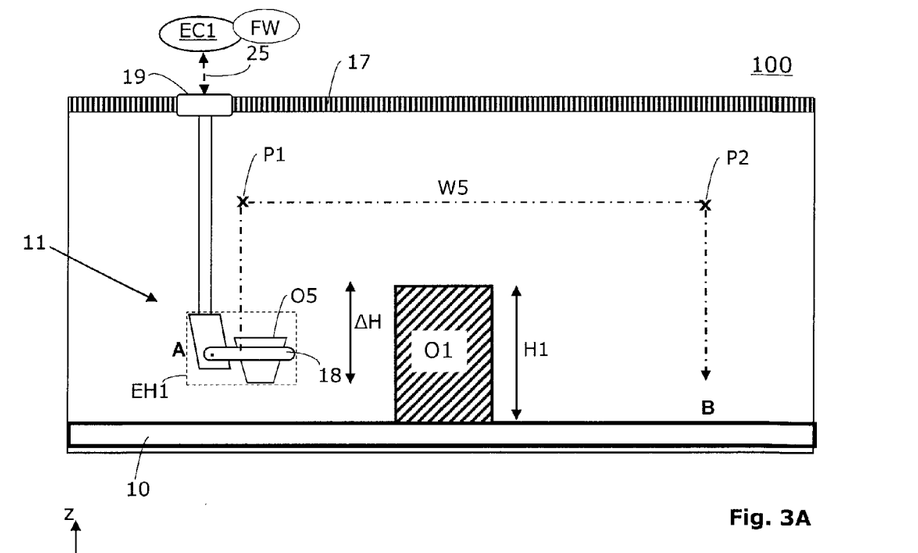
FIG. 3A shows a schematic side view of a further handling system of the invention, wherein only one arm and one container is shown.

Rule4: The movement planning algorithm of the invention is preferably working in all embodiments with the Rule4, which requires that z-movements are not only simple lifting movements parallel to the z-axis but are instead to be carried out as sloping movements. This Rule4 is named here for simplicity the trapeze rule. Rule4 may be used together with or as an alternative to Rule3. In the FIGS. 3A and 3B, Rule4 is illustrated by use of a schematic example. In FIG. 3A, a system 100 of the invention is shown in a side view. The x-y planes are arranged vertically to the drawing plane. A first arm which is movable e.g. along a bridge 17 in x-direction (shown is a portal or bridge system) comprises e.g. a gripper 18 which carries a liquid container O5 at the time point shown. For modelling the arm 11 in the system 100, he was defined by an enveloping body (here a 3-dimensional rectangle as envelope EH1).

The trapeze rule may require in all embodiments of the invention another course of the path as well. For example a pure lifting movement parallel to the z-axis may develop to a slightly slopy movement and then to a subsequent x- or y-movement.

Now, the above described Rule1 is preferably applied. The height H1 (max_height in z-direction) of the highest object O1 in the working area 10 is identified. Then, the height difference ΔH between the current starting point A of the arm 11 on the z-axis and the height H1 is determined. This height difference ΔH is then set as a waypoint P1 for the movement planning (e.g. in step S2 of FIG. 2A). In case the envelope EH1 does not comprise a security distance, a small Δz may be considered as a security distance when defining the waypoint P1.

The provision of a security distance may optionally be defined as an additional Rule5 in the movement planning algorithm MPA.

Then the maximal travelling distance in x- and/or in y-direction may be identifies for finding the waypoint P2. A vertical lowering of the arm 11 from the waypoint P2 would then lead to the destination B. The collision examination CE in the example shown in FIG. 3A would give a negative result [KP=0] as no collision would occur when driving the arm 11 along the path W5.

Figure 3B:
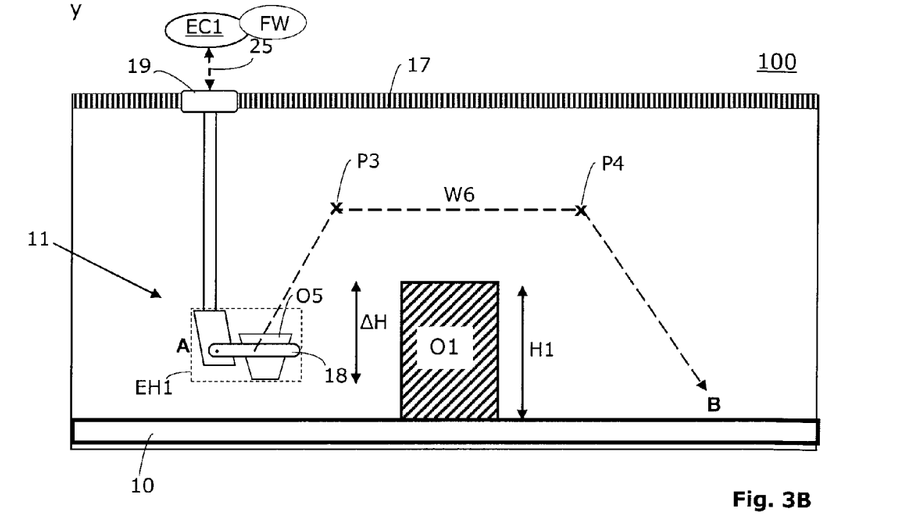
FIG. 3B shows a schematic side view of the handling system of FIG. 3A.

Rule4 might now provide that instead of the pure lifting and lowering movements (parallel to the z-axis, as shown in FIG. 3A), so-called ramp movements are preferred. FIG. 3B shows a planning of a path with ramp movements, starting from the same constellation as shown in FIG. 3A. When determining the waypoint P3, again the difference in height ΔH might be considered (eventually with a security distance in addition), by using Rule1. Between the waypoint P3 and the waypoint P4, at which a ramp-type lowering movement starts, it is not the maximal travelling distance in x- and/or y-direction which is covered, but instead, the distance between P3 and P4 is chosen to be shorter than the distance between P1 and P2 in FIG. 3A. By a slopy lowering of the arm 11 from P4 to the destination position B, the final target position is reached. It is an advantage of the path planning according to FIG. 3B that the path W6 is shorter than the path W5.

The trapeze rule (Rule4) or modifications of this trapeze rule may be used in all embodiments for shortening movements in z-direction and/or in x-direction and/or in y-direction. This means that the trapeze rule(s) may be used in all dimensions which are possible based on the degree of freedom or the movability of the arms, respectively.

As a further heuristic rule, the so-called Rule6 for the smallest possible rotation may be used in all embodiments. This Rule6 will be described by reference to the FIGS. 4A, 4B and 4C, wherein these figures as well are solely schematic nature.

A part of the rules (e.g. the trapeze rule (Rule6)) may be defined in the firmware FW or in the profile generator. In this case the respective rules are not part of the set of rules of the movement planning algorithm MPA.

Figure 4A:
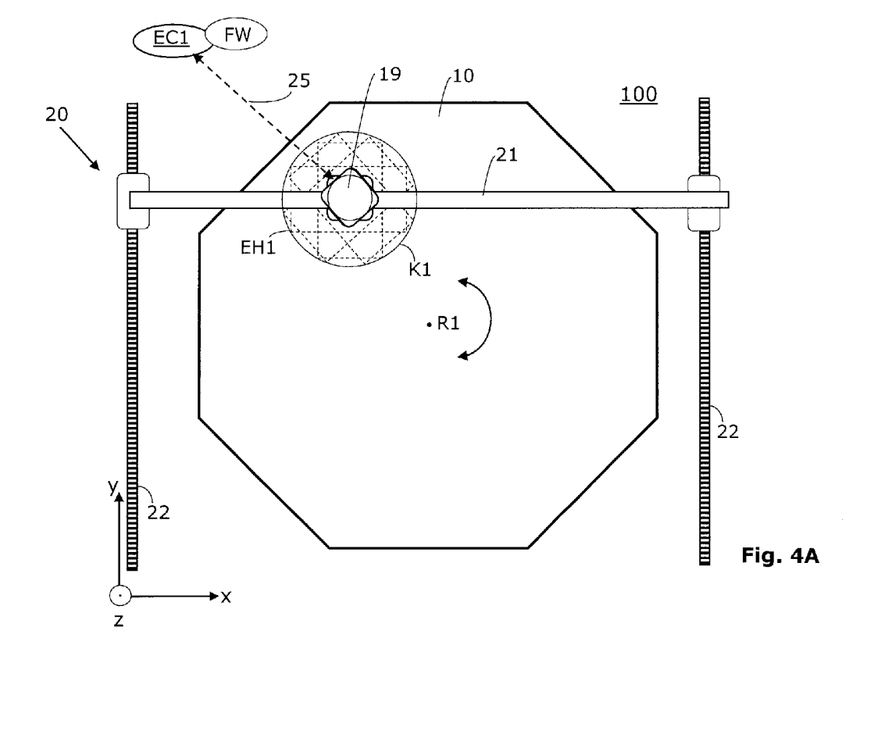
FIG. 4A shows a schematic top view on a further handling system of the invention, wherein only one arm is shown.
Figure 4B:
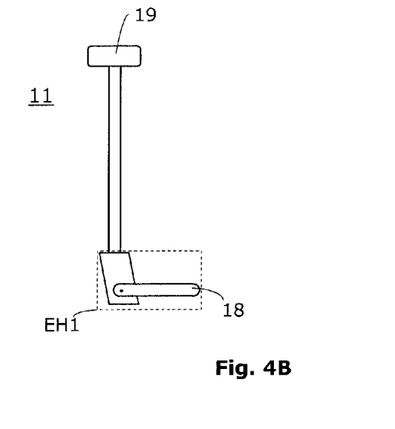
FIG. 4B shows a schematic side view of the one arm in FIG. 4A in a standby condition.
Figure 4C:
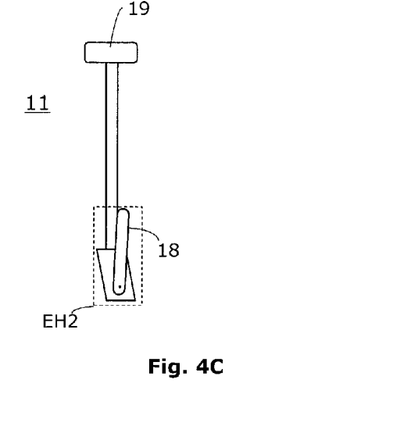
FIG. 4C shows a schematic side view of the one arm in FIG. 4A in a swing-in condition.

FIG. 4A shows as FIG. 1 a top view on the working area 10 of a system 100. FIG. 4B and FIG. 4C each show a side view of the arm 11 of FIG. 4A in an isolated presentation. The working area 10 here takes the form of an octagon. Central element of this system 100 may be an octagonal plate which rotates around a central z-axis R1, as indicated by the double arrow. Laterally and/or above the working area 10 may be arranged several guide rails/bridges 17 which serve as a guidance for the arms 11, 12. In the example shown rails on each side of the working area 10 are provided. A portal 20 having a horizontal bridge 21 is movable parallel to the y-axis along the rails 22. A carriage 19 is movable along the horizontal bridge parallel to the x-axis. The carriage 19 here is part of the first arm 11 which comprises a gripper. This type of arrangement is a further example for possible constellations of handling systems 100.

The envelope EH1 of the gripper 18 of the arm 11 is modelled in FIG. 4A by a rectangle (as in the FIGS. 3A, 3B). In FIG. 4A the envelope EH1 is shown in different rotary positions to indicate that the corners of the envelope EH1 over-sweep a circular space K1 when rotating around the z-axis. Such an arm 11 which has an asymmetric structure in relation to its z-rotation axis, over-sweeps a relatively big circular space K1 when rotating. The Rule6 of the smallest possible rotation may comprise one or more of the following default settings/partial rules:

A. Rule 6.1: The arm 11 may be moved out of the working area 10 for rotation around the z-axis, or at least moved to the boarder of the working area 10.
B. Rule 6.2: The perimeter of the arm 11 may be reduced prior to the rotation for reducing the radius of the circle K1. This principle is illustrated by a comparison of the FIGS. 4B and 4C. In FIG. 4C, the arm 11 is shown with the gripper 18 being folded up. By raising the gripper 18, the whole arm 11 is protruding less within the x-y-plane. An envelope EH2 results which has a considerably reduced area in the x-y-plane and which has a considerably smaller turning circle in the x-y-plane.
C. Rule 6.3: Other rotational movements and/or combinations thereof may be provided by Rule 6.3, so that an arm 11 or 12 may e.g. be lifted parallel to the z-axis to only rotate said arm in a higher position (in the free air space).

There may be few constellations where the movement planning algorithm MPA does not provide a result. To dissolve such a situation, in all embodiments may e.g. the following heuristic Rule7 be provided:

X1. Analyze whether another arm 11, 12 present may carry out the desired movement/action, which is required by the first movement request MR1, in the system. This analysis according to X1 may then lead to a result if the system 100 comprises at least two identical or similar arms. Within this analysis, the path planning and the collision examination will be carried out for this other arm;

X2. In case step X1. does not solve the situation, one of the objects O1-O4 might be grabbed from the working area 10 and positioned on another position. In the example shown in FIG. 1, due to this reason the object O4 thus might already be located within an evasion area 16. After repositioning one or more of the objects O1-O4, the path planning and collision examination might be carried out again.

X3. In most of the cases, the steps X1. or X2. indeed solve the situation. In an emergency a signal might be given for alerting the user of the system 100 to a situation which is not solvable.

As a further Rule8 in the heuristic approach, in all embodiments a time limit may be provided. By the restriction of the planning time e.g. to ten seconds it may be avoided that the pathfinding takes too much time. In case the time limit is reached, e.g. one of the steps X1., X2. or X3 may be carried out to anyhow find a path. In the embodiment according to FIG. 2C, instead of the number M, instead a time limit may be given as default. When reaching the time limit, then the process 200.1 is finalized and the process 200.2 follows.

The heuristic approach of the invention uses, where possible and reasonable, the knowledge present in the system 100. On the one hand, the heuristic approach of the invention uses the knowledge on the current topography (here named as actual topography), and on the other hand uses the rules (e.g. one or more of the Rules1 to Rule13). By this it is avoided that in the planning of the movement, the software virtually methodless considers several points within the area and, after an unsuccessful collision examination CE has to reject them.

The heuristic approach uses simple rules (e.g. one or more of the Rules1 to Rule13) which are provided by the system or which are providable, to find to a solution as fast as possible.

The system 100 is characterized in that the topography of the working area 10 may be changed from time to time, as one particular object (e.g. the at least one liquid container O1) may be placed on the working area 10 at different positions. Thus, prior to each path planning the actual topography is determined or is retrieved from a storage. The actual topography is considered as being quasi-static in case no or only negligible changes of the actual topography occur during the time of a movement of an arm 11,12.

To guarantee a problem-free movement of the two arms 11, 12, a control module C is used which may carry out the required steps (e.g. the steps of the process 200). This control module C may be part of the system 100, or it may be accomplished as a separate module which is connected with the system 100 by way of communication techniques (e.g. by an interface 24), as already described.

The control module C preferably is in all embodiments implemented as a software solution or as a combination of hardware and software, as well known. A storage 13 (internal or external) may be assigned to the control module C, as indicated in FIG. 1. The control module C and/or the system 100 may comprise an interface 23 by which e.g. rules in the form of data or signals may be transmitted.

In all embodiments the movement planning algorithm MPA and the collision examination CE may be implemented into the control module C, as indicated in FIG. 1.

The control module C determines or loads (e.g. from a storage) in a preparatory step the current quasi-static actual topography of the working area 10, including the at least one object O1. In case of the exemplary embodiment of FIG. 1, not only the envelopes of the object O1, but additionally the envelopes of the other objects O2, O3, and O4 are considered in the actual topography.

Then, a first movement request MR1 for a first of the two arms 11 is provided to the system 100, wherein this movement request orders a movement from a first position A to a second position B. Such a movement request MR1 may be generated in all embodiments of the invention out of the system 100, or may be provided e.g. by an external control or application software.

The system 100 and/or the control module C then determines the shortest path W1 from the first position A to the second position B by use of the movement planning algorithm MPA. In FIG. 1, the shortest path W1 is a straight line which directly leads from position A to position B. Alternatively, in this first step, another reference path may be used instead of the shortest path W1 (e.g. the path W5 in FIG. 3A).

Now, a collision examination CE is carried out by the system 100 and/or the control module C, for determining whether the first of the arms 11 would collide with the actual topography of the working area 10 when being moved along the shortest path W1 or along another reference path.

FIG. 1 reveals that a direct movement of the arm 11 along the shortest path W1 would result in a collision with the object O2 (in this example it is assumed that the third dimension, which is vertical to the working area 10, does not provide space for evasion). The collision examination CE may thus end e.g. with the issuance of the result CE=1.

As the result for the path W1 is CE=1, no adjustment with other moving arms (e.g. with arm 12) is necessary. In case the collision examination CE of the path W1 would give the result CE=0, then in a second step a collision examination CE might be carried out with considering other moving arms. This means that the steps S4.3, S5.1 and S6 e.g. of the process 200 according to FIG. 2B do not need to be carried out.

A dynamic collision examination CE may be carried out in a collision examination CE by considering other moving arms in the system 100 and/or the control module CE, for determining whether the first arm 11 would e.g. collide with the second of the arms 12. In the example shown, the second arm 12 is seated above and outside of the working area 10. This dynamic collision examination CE, if carried out at all, would therefore result in CE=0.

The system 100 and/or the control module C then carries out a default/reference movement W1 or an evasion movement W2, W3, W4 of the first of the two arms 11, for moving it from the first position A to the second position B. The decision over the path the movement shall follow is taken in dependence from the result of the collision examination CE. As the shortest path W1 is obstructed (CE=1), an evasion movement must be found by repeating the steps (in FIG. 2A, e.g. the steps S2, S3, (S4.1), S4, S5 are repeated; in FIG. 2D, the steps S3.1, S3.2, S5 are repeated) and then carried out.

In FIG. 1, three possible evasion movements W2, W3 and W4 are shown, all of them being composed of a sequence of linear partial movements. The evasion movement W2 comprises a short movement in y-direction, a longer movement in x-direction and an additional shorter movement in y-direction. The evasion movement W3 comprises a movement in y-direction and a longer movement in x-direction. The evasion movement W4 comprises a short movement in negative y-direction, a longer movement in x-direction and an additional movement in y-direction. The evasion movements W2 and W3 would lead to collisions with the objects O2 or O1. These evasion movements W2, W3 are therefore not available (CE is in both cases equal to "1"). The evasion movement W4 on the other hand does not result in a collision (CE=0), and the system 100 and/or the control module C may drive the first arm 11 or the motor control MC1, respectively, that this arm 11 carries out the evasion movement W4.

In all embodiments, the third dimension (here the z-direction) may be taken into account as well. In case the system 100 provides enough space above the working area 10, an object O2 might be overcome e.g. by lifting of the arm 11 so that there will be no collision. In this case, the corresponding evasion movement would comprise a stroke movement in z-direction and eventually at the end of the movement a lowering movement into a negative z-direction. If e.g. Rule4 is applied, then the arm 11 carries out so-called trapeze movements.

In all embodiments an approach might be used where in a first row the movement planning MPA and the collision examination CE are carried out for a first lower plane. This first cycle of movement planning MPA and collision examination CE is quasi 2-dimensional and considers particularly the objects O1-O4 in the working area 10 and the movement of the arm 11 in the x-y plane around these objects. The initial use of the movement planning algorithm MPA and collision examination CE in 2 dimensions might be regulated e.g. under a Rule9.

In a second cycle of the movement planning MPA and collision examination CE, then the working space above the working area 10 might be taken in to account (named here Rule10). In this way, by combining e.g. Rule10 with Rule9, a suitable path might be found relatively fast, if the working space above the working area 10 is free.

Preferably, in all embodiments such a Rule10 is used, as this Rule10 gives considerably more often paths which are free of collisions compared to Rule9.

In all embodiments, the three-dimensional shape of the movable arm 11 and/or of the objects O1-O4 might be taken into account as well. In this way, e.g. an arm 11 which is particularly projecting into one direction, might be rotated around the z-axis (e.g. by applying Rule6) so that the arm 11 may be moved without problems around an object O1-O4.

Preferably in all embodiment each direct or indirect movement of an arm 11, 12 is divided into small increments. For each of these single points which so arise in the path planning MPA along a path, a collision examination CE is carried out. Thus, virtually the arm 11,12 is moved step by step over the working area 10 and through the working space above the working area 10, and increment by increment a collision examination CE is carried out for finding contacts or penetrations.

If none of the objects O1-O4 will be moved within the time frame which is used to cover the distance of the direct or indirect paths W1-W4, and if none of the other arms (e.g. arm 12) will carry out a movement within this time frame, then a simple quasi-static collision examination CE (e.g. in a step S4.2 of FIG. 2B) may be carried out based on the actual topography.

However, if there will be additional movements in the system 100 within said time frame, then in addition to the spatial coordinates also a time aspect will be included into the collision examination CE. For this purpose, e.g. a dynamic collision examination CE is carried out additionally; see e.g. step S4.3 in FIG. 2B. An evasion movement which is determined accordingly then comprises a time component as well.

In all embodiments, the system 100 and/or the control module S may, in a simple case, calculate with a uniform movement along a path. This means in this case a movement is assumed to be carried out with a constant speed, and neither the acceleration phase nor the deceleration phase will be taken into account. A path which shall be examined arithmetically by the collision examination CE is in each case divided into small time increments. Point by point e.g. the arm 11 is moved along such a path and it is examined for each point and for each time point whether a collision might occur. The assumption of a movement with a constant speed is particularly suitable for the quasi-static collision examination CE, as here, no proper movement of one of the objects O1-O4 is to be expected.

However, a motion profile is preferably in all embodiments included into the considerations (e.g. given by a firmware of a profile generator), said motion profile comprising an acceleration phase, a constant movement phase and a deceleration phase. Here, preferably in all embodiments the firmware FW or the profile generator of each drive is taken into account, as described further below.

In all embodiments which work with a providable acceleration and/or speed and/or negative acceleration (deceleration), the corresponding parameters may be assigned to at least one of the arms 11, 12. These parameters will then be considered in the collision examination CE, as they provide a dependency of the respective position of the arm 11 in the space.

The system 100 and/or the control module C may in all embodiments divide during the collision examination CE a theoretically suitable path either into equidistant sections (step width), or it may divide a path into (uniform) time sections. When assigning required step widths and/or time sections, the size of the objects O1-O4 should be taken into account, so that no object is missed out or overseen when analyzing for potential collisions. The invention relies on a discrete (stepwise) collision examination CE to thereby optimally profit from the processing power available.

The width of steps may be adjusted to the respective situation.

If the collision examination CE indicates a collision which is to be expected (CE=1), an evasion path is provided (e.g. steps S2 and S3 in FIG. 2A), and the collision examination CE (steps S4, S5 in FIG. 2A) is repeated based on this evasion path until finally a path is found within the spatial and temporal regime which is free of collisions, thus, until in step S5 of FIG. 2A or in step S5.1 of FIG. 2B the result is CE=0.

If the collision examination CE indicates a collision which is to be expected (CE=1), the "parking" of one of the arms 11, 12 in an evasion position may be required in all embodiments (Rule11). One of the arms 11, 12 is virtually put into this evasion position, and then the pathfinding and the collision examination CE, or the collision examination CE only are repeated.

If an arm which has temporarily been "parked" in an evasion position has to execute a certain function, then in a subsequent step an new path has to be calculated, wherein this calculation then assumes that the evasion position is the starting point. For this arm the process 200 is applied then as well.

If in a system 100 with two moving arms 11, 12 (and/or a moving object O1-O4) a potential collision is detected in the dynamic or in the combined collision examination CE of a path, then as a countermeasure it is simulated by way of calculation whether the collision may be avoided when the movement of the first arm 11 in relation to the second arm 12 (and/or to an object O1-O4) is staggered in time. This first countermeasure may be defined as Rule12.

A movement staggered in time may be achieved, by either
start moving the arm 11 delayed in time, and/or
start moving the arm 12 delayed in time, and/or
move one of the arms 11, 12 not as fast, and/or
move one of the arms 11, 12 faster.

For this as well respective rules (partial rules) may be provided in the system 100.

All embodiments which work with a time staggering when a collision is to be expected (Rule12), preferably a prioritization is used (Rule13). By applying a prioritization, e.g. one arm 11 may be preferred over the other arm 12. In case the arm 11 e.g. is productively used for pipetting a serum into a liquid container O1, the movement of the arm 12 may be delayed in time if it has a lower priority. Alternatively, the path of the arm 11 may be set as being fix when finding a path for the arm 12.

Preferably in all embodiments a movement planning algorithm MPA is used which comprises a set of rules with multiple rules (e.g. the Rules1 to Rule13), the rules being heuristic. The movement planning algorithm MPA and/or the set of rules, respectively, generate a process connection between the single rules. Such a process connection provide specifications to the system 100 on how to decide in certain situations. For this the movement planning algorithm MPA may comprise e.g. a process connection which is described in the following in form of a pseudo-computer language.

Implementation of the movement planning algorithm MPA by way of example when a movement request (MR1) from A→B is provided:
Setting waypoints for the shortest path from A→B
Connecting waypoints to a path
Carrying out collision examination CE (quasi-static and/or dynamic or combined)
If CE=0 then output data for the first path
Otherwise execute loop 1
[Loop 1]
Applying a rule from the set of rules for finding (other) waypoints
Connecting waypoints to (another) path
Carrying out collision examination CE (quasi-static and/or dynamic or combined)
If CE=0 then output data for the (other) path
Otherwise go back to the beginning of loop 1.

It is obvious that there are different possibilities to implement a movement planning algorithm MPA in such a way that it may allow the automated path planning and finding in a system 100.

A conditional connection of the rules of a movement planning algorithm MPA may e.g. be accomplished as follow. It has to be mentioned here that the following example shall merely present the general principle of a connection.
Use of Rule1
If the result is CE=1, then use of the Rule2
Otherwise, use of the Rule3.

After executing a collision examination CE preferably in all embodiments a data set is outputted which is usable for activating/moving the arm(s) 11, 12. Such a set of data may comprise in all embodiments e.g. a vectorial description of the single movements, or each path may be defined as an assembly of single triple-coordinates, or each path by be described by the position on the axes. For each path parameters may optionally be provided, as described, which specify accelerations, speed and optionally prioritizations. These movement characteristic however may be defined as well by firmware FW or the profile generator of the respective engine controls EC1, EC2.

The respective movement(s) is/are then carried out in the system 100.

In case that during the execution of the respective movement(s) in the system 100 a further movement request MR2 is entered, it is tried in a first step to find a path for this further movement request in the collision examination CE, which does not collide with the current movement. This means it is tried to find a path for the further movement which leads through the already moving elements (arms and/or objects) without collisions. For that the already ongoing movements are preferably not interrupted or re-guided, that is the first movement request MR1 is executed completely (assumed to be unchangeable).

Preferably in all embodiments, objects O1-O4 (static, quasi-static) and (dynamic) arms 11, 12 are modelled or defined mathematically by an envelope EH1, EH2 in the system 100 and/or control module C. Preferably, these objects O1-O4 and arms 11,12, respectively their mathematical model, are stored in a library (e.g. in a storage 13).

Preferably in all embodiments, the mathematical models of the respective objects O1-O4 and arms 11, 12 are aligned with the basic axes of the system 100, thereby minimize the required storage space and computing time.

Preferably in all embodiments a minimum distance for each of the objects is specified in the library.

According to the invention the application of the movement planning algorithm MPA and the collision examination CE is retrieved and executed as soon as a movement request MR1, MR2 for one of the arms 11, 12 is provided to the system 100 or is generated in the system 100.

Preferably the invention is implemented in all embodiments as follows:

- Collision free path finding (planning of a path according to movement planning algorithm MPA, followed by a collision examination CE) for movement(s) of the arms 11, 12: For a movement of an arm 11 a path shall be found which does not result in collisions with the working area 10, with the objects O1-O4 placed onto the working area 10, or with another arm 12.
- Simultaneously evading of an uninvolved arm 12: an arm 12, which is positioned in the way of a potential path of an arm 11 and which currently does not execute an action, is to execute an evasion movement simultaneously to the actual movement, thereby clearing the path (e.g. by use of the Rule11).
- Execution of critical actions without disruption: a possibility should be provided which ensures that arms which currently execute an action, e.g. pipetting, are not moved for e.g. evading another movement in the system 100.
- Simultaneous movement of multiple arms 11, 12 without collision: Multiple arms 11, 12 shall be movable independent from each other, provided that they do not hamper each other. For this, paths must be generated simultaneously which do not result in collisions between the moving arms 11, 12. Corresponding planning of the paths and collision examinations may be carried out in parallel (see e.g. FIG. 2B) or in alternating steps.
- Fast calculation of a path: The actual (productive) movement of an arm 11 from the one side to the other side of the system 100 typically takes only a few seconds. The planning of a path MPA and the collision examination CE of a path may require only a short time (preferably a few seconds) to not reduce the productivity of the system 100.
- Finding of the fastest path: Each unnecessary movement reduces the throughput of probes, thus, the productivity of the system 100, respectively. As the systems 100 often are configured for a high throughput, preferably the fastest paths have to be determined.
- Reproducibility of the paths: In cases where the same starting point A and end point B are used multiple times for planning, each path planning MPA and collision examination CE must generate the same path. This is necessary for ensuring that the system 100 is working correctly. This is of particular importance in the area of laboratories, as here the systems 100 must be validated; this requires the predictability of the generated paths.

In the claims, the process steps of the process 200 are partly furnished in form of a list with letters. The resulting sequence of the single steps is not mandatory. The steps may be carried out partly in another sequence and partly overlapping in time.

REFERENCE SIGNS

| | |
|---|---|
| Working area | 10 |
| First (handling)arm | 11 |
| Second (handling)arm | 12 |
| Storage | 13 |
| Blocked area | 14 |
| Liquid tank | 15 |
| Evasion area | 16 |
| Guiding rail/bridge | 17 |
| Gripper | 18 |
| Carriage | 19 |
| Portal | 20 |
| Horizontal bridge | 21 |
| Rails | 22 |
| Interface | 23, 24 |
| Wire(s) | 25 |
| Liquid handling system | 100 |
| Process | 200 |
| Partial steps of the process | 200.1, 200.2 |
| Loops | 201, 202, 203 |
| Branches back | 204, 205, 206, 207 |
| Table | 210 |
| First Position | A |
| Algorithms | MPA, Algo1, Algo2, Algo3 |
| Second Position | B |
| First movement request | MR1 |
| Second movement request | MR2 |
| Movement planning algorithm | MPA |
| Data/Output quantity | Data1, Data2 |
| Envelope | EH1, EH2 |
| Firmware | FW |
| Image of the Firmware | FW* |
| Height | H1 |
| Height difference/relative evasion height | ΔH |
| Circle | K1 |
| Collision examination | CE |
| Collision examinations | CE.1, CE.2 |
| Engine control | MS1, MS2 |
| Objects (e.g. liquid container) | O1, O2 O3, O4, O5 |
| Priority switch | p |
| Waypoints | P1, P2 ... |
| central z-Axis | R1 |
| Controller/control module | C |
| Steps | S1, S2, S3, S4, etc. |
| Steps | S2.1, S2.2, S2.3, S2.4 |
| Steps | S4.1, S4.2, S4.3 |
| Step | S5.1 |
| (process)point | V1; V2 |
| First path | W1 |
| Second path | W2 |
| Third path | W3 |
| Fourth path | W4 |
| Fifth path | W5 |
| Sixth path | W6 |
| Coordinates | x, y, z |
| Steps | X1, X2, X3 |

The invention claimed is:

1. Process (200) for collision avoidance in an automated handling system, which comprises:
   a working area (10) which is configured for quasi-static receiving of at least one object (O1),
   at least two numerically controlled arms (11, 12) which are movable above the working area (10),
   wherein the following steps are carried out:
   a. Providing the actual topography of the working area (10) including the current position of the at least one object (O1),
   b. Providing (S3.1; S2, S3, S4.1) a path from a first position (A) to a second position (B), wherein when this step b is passed through for the first time, a reference path, preferably the shortest path (W1) is provided as a path, c. Executing a quasi-static collision examination (S4, S5; S4.2) for the provided path (W1), for determining whether the first of the two arms (11) would collide with the actual topography of the working area (10) when being moved along this path (W1), d. Repeating the steps b., c. and d. as long as in step c. a collision is detected, otherwise executing the subsequent step e., e. Executing a dynamic collision examination (S4, S5; S4.3, S5.1) for the path (W1), for determining whether the arms (11, 12) would collide with each other in case the first arm (11) would move along this path (W1);

f. Applying an evasion strategy if a collision was determined in step e., and executing a movement of the first arm (11) from the first position (A) to a second position (B) by applying the evasion strategy;

g. Executing a movement of the first arm (11) from the first position (A) to the second position (B) along the path (W1) if the dynamic collision examination in step e. has not determined a collision.

2. Process according to claim 1, wherein with each run through the step b. in each case another possible path from the first position (A) to the second position (B) is determined (S2, S3; S4) and provided, wherein the determination of further possible paths is based on a set of rules.

3. Process according to claim 2, wherein in step b. other possible paths which leads from the first position (A) to the second position (B) are taken from a table or list (219) (S3.1).

4. Process according to claim 3, wherein in a preparatory step (S2.2) multiple possible paths are determined by use of a set of rules and stored in the table or list (210).

5. Process according to claim 1, wherein
i) the movement of the first of the two arms (11) from the first position (A) to the second position (B) is carried out along the reference path if the first passing through the step c. did not result in a collision,
ii) the movement of the first of the two arms (11) from the first position (A) to the second position (B) is carried out along an evasion path which has been determined by use of the evasion strategy, if passing through the step e. resulted in a collision.

6. Process according to claim 5, wherein
in step ii) in addition to the movement of the first of the two arms (11) along the evasion path, the second of the two arms (12) is moved along an evasion path as well, or
in step ii) the first of the two arms (11) is moved along the reference path and the second of the two arms (12) is moved along an evasion path, or
in step ii) a movement of the first of the two arms (11) is carried out staggered in time relative to the second of the two arms (12).

7. Process according to claim 1, wherein both arms (11, 12) are movable simultaneously above the working area (10).

8. Process according to claim 1, wherein when providing the actual topography, the at least one object (O1) as well as other static and quasi-static objects are modelled or defined mathematically by an envelope (EH1, EH2) in the handling system (100) and/or controller (C).

9. Process according to claim 1, wherein when applying the evasion strategy in step f. a set of rules is applied.

10. Process according to claim 2, wherein the set of rules comprises one or more heuristic rules.

11. Process according to claim 2, wherein the set of rules comprises one or more of the following rules:

Determining a relative evasion height (ΔH) which is suitable for moving one of the arms (11, 12) above one of the objects (O1) without collision (Rule1);

Excluding a blocked area (14) (Rule2);

Considering of all technically possible movements of the arms (11, 12) in the handling system (100) (Rule3);

Avoiding of pure stroke movements and/or pure lowering movements when carrying out an evasion movement (W2, W3, W4) (Rule4);

Providing a security distance prior to the execution of an evasion movement (W2, W3, W4) (Rule5);

Providing a smallest possible rotation if one of the arms (11, 12) shall carry out a rotational movement (Rule6);

Examine if another than the arm addressed in the first movement request (MR1) might carry out the outstanding handling or movement (Rule7 X1);

Examine whether the object (O1) in the working area (10) may be picked up and positioned at another position (Rule7 X2);

Outputting a signal for advising a user of the handling system (100) of a situation which is not solvable (Rule7 X3);

Providing a time limit and use of another Rule (Rule8);

Initial determination (S2, S3; S4.1) of a path in 2-dimensions (Rule9);

Executing the determination (S2, S3; S4.1) of a path in a working space above the working area (10) (Rule10);

Parking of one of the arms (11, 12) in an evasion position (Rule11);

Examine whether a movement of the first arm (11) may be carried out staggered in time relative to the second arm (12) (Rule12);

Applying a prioritization to favor one of the arms (11) over the other of the arms (12) with respect to time or path (Rule13).

12. Process according to claim 1, wherein within the scope of one of the partial steps the image of a firmware (FW*) is used, to determine a path more accurate and to carry out the collision examination(s) of the step(s) c. and/or e. based on this more accurate path.

13. Process according to claim 12, wherein for each of the two arms (11, 12) an image of another firmware is used.

14. Process according to claim 1, wherein in the scope of one of the partial steps a profile generator is used for determining a more accurate path, wherein the profile generator is also used for controlling the execution of a movement of the first of the two arms (11) from the first position (A) to the second position (B).

15. Automated handling system (100), which comprises:
a working area (10),
at least one object (O1) which is placed in the working area (10),
at least a first numerically controlled arm (11),
at least a second numerically controlled arm (12), wherein these arms (11, 12) are movable above the working area (10),
means for collision avoidance (S, MPA, CE), which are implemented in such a way that
the current actual topography of the working area (10) is determinable,
a movement planning algorithm (MPA) is applicable which determines a path from a first position (A) to a second position (B), wherein in the first application of the movement planning algorithm (MPA) a reference path, preferably the shortest path (W1) is provided as a path, a quasi-static collision examination (CE) for the path (W1), which has been provided by the movement planning algorithm (MPA), is applicable, a dynamic collision examination (CE) for the path (W1), which has been suggested by the movement planning algorithm (MPA), is applicable, wherein the quasi-static collision examination (CE) is configured to determine whether when moving the first arm (11) from the first position (A) along the path to the second position (B) a collision would be provoked, and wherein the dynamic collision examination (CE) is configured to determine whether when moving the first arm (11) and the second arm (12) a collision would be provoked.

16. Automated handling system (100) according to claim 15, wherein in each case one possible path from a first position (A) to a second position (B) is determinable (S2, S3; S4.1) and then the collision examination (CE) of this possible path is carried out, wherein the determination of possible paths is based on a set of rules.

17. Automated handling system (100) according to claim 15, wherein multiple possible paths are retrievable from a table or list (210), for examining by the collision examination (CE) one path after the other, until a collision-free path was determined.

18. Automated handling system (100) according to claim 15, wherein a set of rules is provided to the handling system (100) which is usable for determining the multiple possible paths.

19. Automated handling system (100) according to claim 15, wherein one or more heuristic rules are providable to the handling system (100) for use, wherein these rules are stored in a storage (13) of the handling system (100) or are transferable via an interface (23) to the handling system (100).

20. Automated handling system (100) according to claim 15, wherein the movement planning algorithm (MPA) and/or the collision examination (CE) is/are implemented into a control module (C), wherein the control module (C) comprises a controller configured to apply the movement planning algorithm (MPA) and/or to carry out the collision examination (CE).

21. Automated handling system (100) according to claim 15, wherein the first arm (11) is controllable by the system (100) by means of an engine control (EC1) in such a way that he carries out movements (W2, W3, W4) to reach the second position (B) when starting from the first position (A).

22. Automated handling system (100) according to claim 21, wherein the engine control (EC1) comprises a firmware (FW) which specifies the movement characteristics of the first arm (11).

23. Automated handling system (100) according to claim 22, wherein an image of the firmware (FW*) is implemented into the control module (C).

24. Automated handling system (100) according to claim 15, wherein it comprises a profile generator which is accessible by the movement planning algorithm (MPA) or which is used in the collision examination(s) (CE).

25. Automated handling system (100) according to claim 15, which is configured to determine a relative evasion height ($\Delta H$), for guiding the first arm (11) collision-free above the container (O1).

26. Automated handling system (100) according to claim 15, wherein by use of a software (MPA) and/or a control module (C) in the determination of a path a blocked area (14) is providable, and/or all technically possible movements of the arms (11, 12) are considerable, and/or instead of pure stroke movements and/or pure lowering movements trapezoidal movements are providable.

* * * * *